(12) United States Patent
Madden

(10) Patent No.: US 12,109,147 B2
(45) Date of Patent: Oct. 8, 2024

(54) METHOD AND SYSTEM FOR AUTOMATION OF PATIENT EYE LEVEL

(71) Applicant: Alcon Inc., Fribourg (CH)

(72) Inventor: Sean Christopher Madden, Mission Viejo, CA (US)

(73) Assignee: Alcon Inc., Fribourg (CH)

( * ) Notice: Subject to any disclaimer, the term of this patent is extended or adjusted under 35 U.S.C. 154(b) by 775 days.

(21) Appl. No.: 17/209,305

(22) Filed: Mar. 23, 2021

(65) Prior Publication Data

US 2021/0298944 A1    Sep. 30, 2021

Related U.S. Application Data

(60) Provisional application No. 63/002,006, filed on Mar. 30, 2020.

(51) Int. Cl.
| | |
|---|---|
| *A61F 9/007* | (2006.01) |
| *A61B 90/00* | (2016.01) |
| *A61B 3/16* | (2006.01) |
| *A61B 34/30* | (2016.01) |
| *A61B 90/25* | (2016.01) |

(52) U.S. Cl.
CPC ............ *A61F 9/007* (2013.01); *A61B 90/361* (2016.02); *A61B 3/165* (2013.01); *A61B 34/30* (2016.02); *A61B 90/25* (2016.02); *A61B 2090/367* (2016.02)

(58) Field of Classification Search
CPC ....... A61F 9/007; A61B 90/361; A61B 3/165; A61B 34/30; A61B 90/25; A61B 2090/367; A61B 3/14; A61B 3/13; G02B 21/0012
See application file for complete search history.

(56) References Cited

U.S. PATENT DOCUMENTS

| | | |
|---|---|---|
| 2011/0251548 A1 | 10/2011 | Thoe |
| 2019/0099226 A1 | 4/2019 | Hallen |
| 2019/0327394 A1* | 10/2019 | Ramirez Luna ....... H04N 23/51 |

FOREIGN PATENT DOCUMENTS

WO    2008098388 A1    8/2008

\* cited by examiner

*Primary Examiner* — James C. Jones
(74) *Attorney, Agent, or Firm* — Patterson + Sheridan, LLC

(57) ABSTRACT

An ophthalmic surgical system includes a robotic arm disposed above a patient's eye. A positioning camera is disposed on the robotic arm and positioned to visualize the patient's eye. A processor is electrically coupled to the positioning camera. The processor is configured to receive an indication of a position of the robotic arm relative to a fixed datum, determine a focal length between the positioning camera and the patient's eye, compare the focal length to the position of the robotic arm, and determine a patient eye level relative to the fixed datum.

19 Claims, 3 Drawing Sheets

METHOD AND SYSTEM FOR AUTOMATION OF PATIENT EYE LEVEL

CROSS-REFERENCE TO RELATED APPLICATIONS

This application claims priority to and benefit of U.S. Provisional Application No. 63/002,006, filed Mar. 30, 2020, the entire content of which are incorporated by reference herein in its entirety.

TECHNICAL FIELD

The present disclosure relates generally to methods and systems for regulating intraocular pressure ("IOP") and more particularly, but not by way of limitation, to a method and system for automated determination of a patient's eye level relative to a fixed datum.

BACKGROUND

This section provides background information to facilitate a better understanding of the various aspects of the disclosure. It should be understood that the statements in this section of this document are to be read in this light, and not as admissions of prior art.

IOP is an important parameter during ophthalmic surgical interventions including, for example, refractive surgery, lens-replacement surgery, and retinal surgery. During surgical interventions, an irrigation fluid is often introduced to the interior of the patient's eye. The flow rate and pressure of the irrigation fluid dictate the resultant IOP. The flow rate and pressure of the irrigation fluid is at least partially dependent on the vertical position of the patient's eye (commonly referred to as "patient eye level"). Thus, an accurate patient eye level determination is required to achieve a desired IOP. Current methods for measuring patient eye level include manual visualization by a surgical technician of the patient's eye relative to an indicator such as a mark or line on the surgical equipment. Such methods of determining patient eye level are subject to parallax error and inefficiencies due to surgical workflow.

SUMMARY

Various aspects of the disclosure relate to an ophthalmic surgical system. The ophthalmic surgical system includes a robotic arm disposed above a patient's eye. A positioning camera is disposed on the robotic arm and positioned to visualize the patient's eye. A processor is electrically coupled to the positioning camera. The processor is configured to receive an indication of a position of the robotic arm relative to a fixed datum, determine a focal length between the positioning camera and the patient's eye, compare the focal length to the position of the robotic arm, and determine a patient eye level relative to the fixed datum.

Various aspects of the disclosure relate to a surgical microscope. The surgical microscope includes a positioning camera positioned to visualize a patient's eye. An encoder is coupled to the positioning camera. The encoder is configured to determine a position of the positioning camera relative to a fixed datum. A processor is electrically coupled to the encoder and the positioning camera. The processor being configured to receive an indication of a position of the positioning camera relative to the fixed datum, determine a focal length between the positioning camera and the patient's eye, compare the focal length to the position of the robotic arm, and determine a patient eye level relative to the fixed datum.

Various aspects of the disclosure relate to a method of determining patient eye level. The method includes focusing a positioning camera on a patient's eye. A position of the positioning camera relative to a fixed datum is determined. A focal length between the positioning camera and the patient's eye is determined. The focal length is compared to the position of the positioning camera relative to the fixed datum and the patient eye level is determined.

This summary is provided to introduce a selection of concepts that are further described below in the detailed description. This summary is not intended to identify key or essential features of the claimed subject matter, nor is it intended to be used as an aid in limiting the scope of claimed subject matter.

BRIEF DESCRIPTION OF THE DRAWINGS

The disclosure is best understood from the following detailed description when read with the accompanying figures. It is emphasized that, in accordance with standard practice in the industry, various features are not drawn to scale. In fact, the dimensions of various features may be arbitrarily increased or reduced for clarity of discussion.

DETAILED DESCRIPTION

Various embodiments will now be described more fully with reference to the accompanying drawings. The disclosure may, however, be embodied in many different forms and should not be construed as limited to the embodiments set forth herein.

Figure 1:
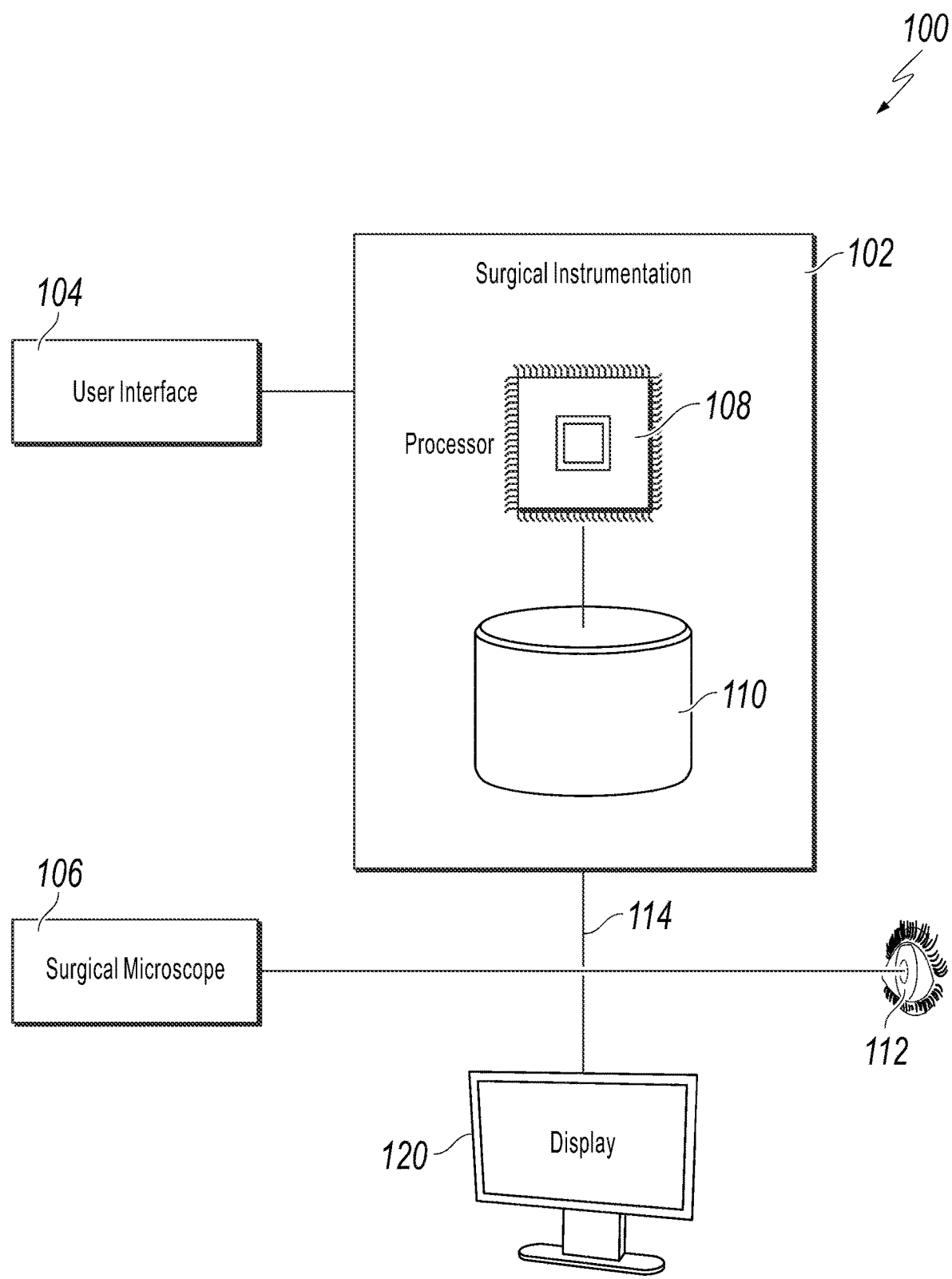
FIG. 1 is a block diagram of an ophthalmic surgical system according to aspects of the disclosure.

FIG. 1 is a block diagram of an ophthalmic surgical system 100. The system 100 includes surgical instrumentation 102, a user interface 104, and a surgical microscope 106. In various embodiments, the surgical instrumentation 102 may include any type of component or machine used in ophthalmic surgical interventions, including but not limited to handpieces, pneumatic systems, laser sources, and illumination sources. The surgical instrumentation 102 may be used in ophthalmic surgical techniques such as, for example, phacoemulsification, vitreoretinal surgery, laser refractive surgery, or any of the other various ophthalmic surgical methods known to one skilled in the art. In various embodiments, the user interface 104 includes any kind of keyboard, switch, knob, pedal, button, pointing device, or other suitable component for receiving selections of surgical parameters from the user. The surgical microscope 106 may include any manner of optical or electronic device or collection of components providing a view of a patient's eye 112 to the surgeon.

The surgical instrumentation 102 operates under the control of a processor 108. The surgical instrumentation 102 also includes a memory 110 that is capable of storing surgical parameter information. The processor 108 may be any microprocessor, microcontroller, programmable element, or other device or collection of devices for processing instructions for the control of the surgical instrumentation 102. The processor 108 receives parameter selections from the user interface 104 and controls the operation of surgical parameters accordingly. The processor 108 also monitors surgical parameters during ophthalmic surgical interventions. The memory 110 may be any suitable form of volatile or non-volatile information storage accessible by the processor 108, including, for example, optical, electronic, or magnetic media.

Still referring to FIG. 1, in various embodiments, the surgical systems 100 includes a display device 120. The display device 120 includes any suitable optical or electronic components or collection thereof capable of generating a visually-perceptible display of surgical parameters on an image of the patient's eye 112. For example, the display device 120 can project light onto a surface of the patient's eye 112 to generate an image that is captured by the surgical microscope 106 along with the image of the eye 112. In other embodiments, the display device 120 can project the display into an optical path of the surgical microscope 106 to produce the display over an image of the eye 112. Such embodiments may allow the display to be focused or magnified along with the image of the eye 112 as well. In other embodiments, the display and image of the eye could be focused or sized independently. In yet another embodiment, the display device 120 can be incorporated into an eyepiece of the surgical microscope 106. The display device 120 may be configured to communicate with and/or share the processor 108 and/or the memory 110 in order to allow the surgical parameter display to be adjusted based on user selection of surgical parameters and variation of those parameters in real time during ophthalmic surgical interventions.

In some embodiments, a data bus 114, which in the illustrated embodiment is a serial bus, couples various components of the ophthalmic surgical system 100 together such that data is communicated therebetween. In a typical embodiment, the data bus 114 may include, for example, any combination of hardware, software embedded in a computer readable medium, or encoded logic incorporated in hardware or otherwise stored (e.g., firmware) to couple components of the ophthalmic surgical system 100 to each other. As an example and not by way of limitation, the data bus 114 may include an Accelerated Graphics Port (AGP) or other graphics bus, a Controller Area Network (CAN) bus, a front-side bus (FSB), a HYPERTRANSPORT (HT) interconnect, an INFINIBAND interconnect, a low-pin-count (LPC) bus, a memory bus, a Micro Channel Architecture (MCA) bus, a Peripheral Component Interconnect (PCI) bus, a PCI-Express (PCI-X) bus, a serial advanced technology attachment (SATA) bus, a Video Electronics Standards Association local (VLB) bus, or any other suitable bus or a combination of two or more of these. In various embodiments, the data bus 114 may include any number, type, or configuration of data buses 114, where appropriate.

Figure 2:
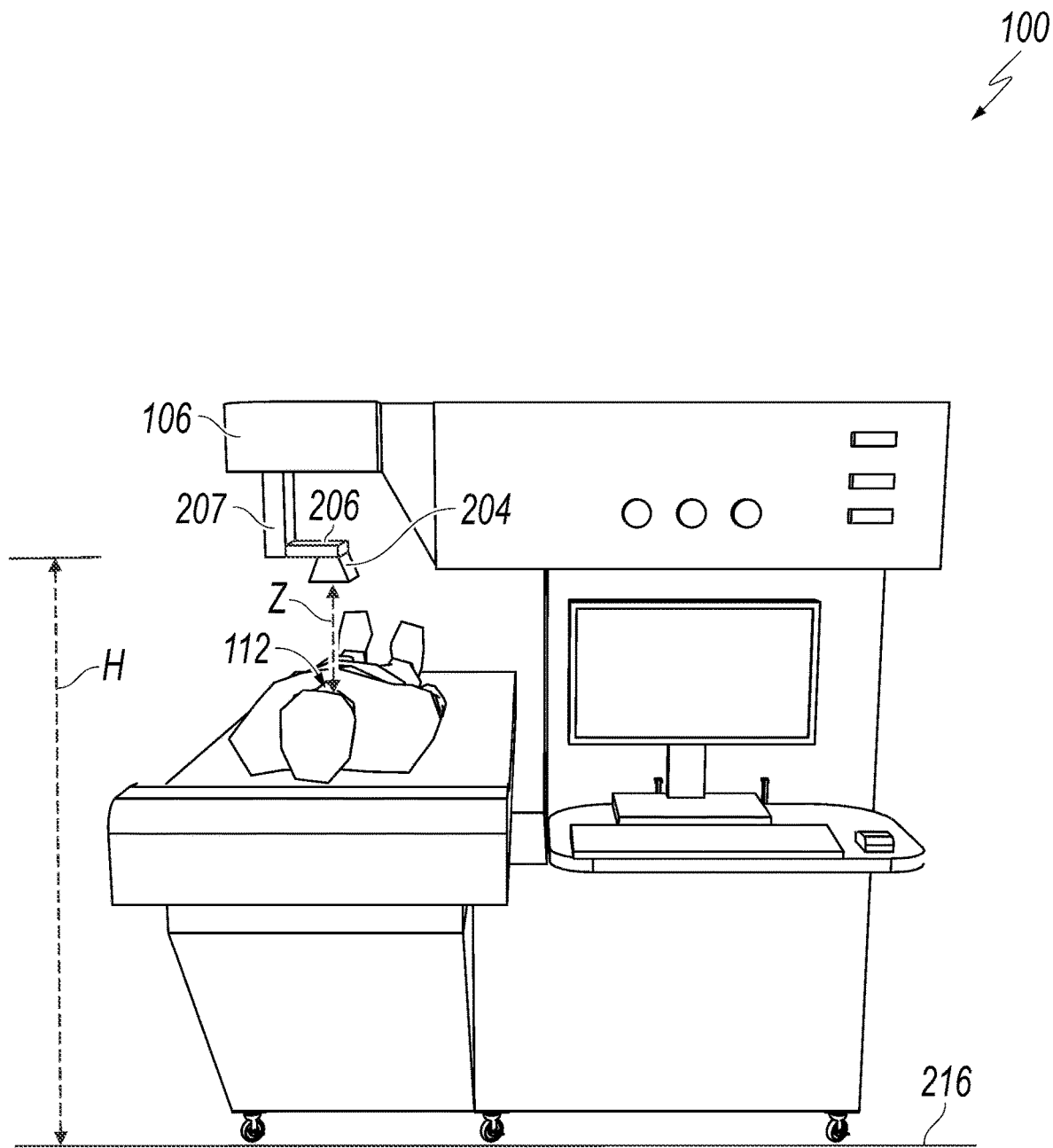
FIG. 2 is a schematic diagram of the ophthalmic surgical system in use according to aspects of the disclosure.

FIG. 2 is a schematic diagram of the ophthalmic surgical system 100 in use. The ophthalmic surgical system 100 includes a positioning camera 204 mounted on a robotic arm 206. In various embodiments, the robotic arm 206 and the positioning camera 204 are positioned below the surgical microscope 106. In various embodiments, the positioning camera 204 is a three-dimensional stereoscopic camera; however, in other embodiments, other types of cameras could be utilized. The processor 108 is electrically coupled to the positioning camera 204 via the data bus 114. The robotic arm 206 is capable of movement such as, for example, vertical translation, horizontal translation, angular movement, and rotational movement. In various embodiments, an encoder 207 such as, for example, a linear encoder or an angular encoder or other similar device is utilized to communicate a vertical position of the robotic arm 206 relative to a fixed datum 216 to the processor 108. In various embodiments, the encoder 207 converts a position of at least one of the robotic arm 206 and the positioning camera 204 into an electrical signal that is able to be communicated to the processor 108.

During operation, the positioning camera 204 is positioned above the patient's eye 112. The encoder 207 communicates a position (h) of the robotic arm 206 relative to the fixed datum 216 to the processor 108. In various embodiments, the fixed datum 116 may be, for example, a floor of a surgical suite; however, in other embodiments, any fixed reference point could be utilized. The positioning camera 204 attempts to focus on the patient's eye 112. The processor 108 determines the focal length (z) between the positioning camera 204 and the eye 112. By comparing the focal length (z) to the position (h) of the positioning camera 204 relative to the fixed datum 216, the processor 108 determines the patient eye level relative to the fixed datum 216. For instance, in the particular case where the fixed datum 216 is the floor of the surgical suite, the difference between the height (h) of the positioning camera 204 above the floor of the surgical suite and the focal length (z) yields the patient eye level. In various embodiments, the patient eye level is determined prior to ophthalmic surgical intervention and is utilized to maintain the desired IOP set point. In other embodiments, the processor 108 continuously determines the focal length (z) of the positioning camera 204 and continuously determines the patient eye level. Continuous determination of the patient eye level facilitates adjustments to IOP due to, for example, repositioning of the patient during the ophthalmic surgical intervention.

Figure 3:
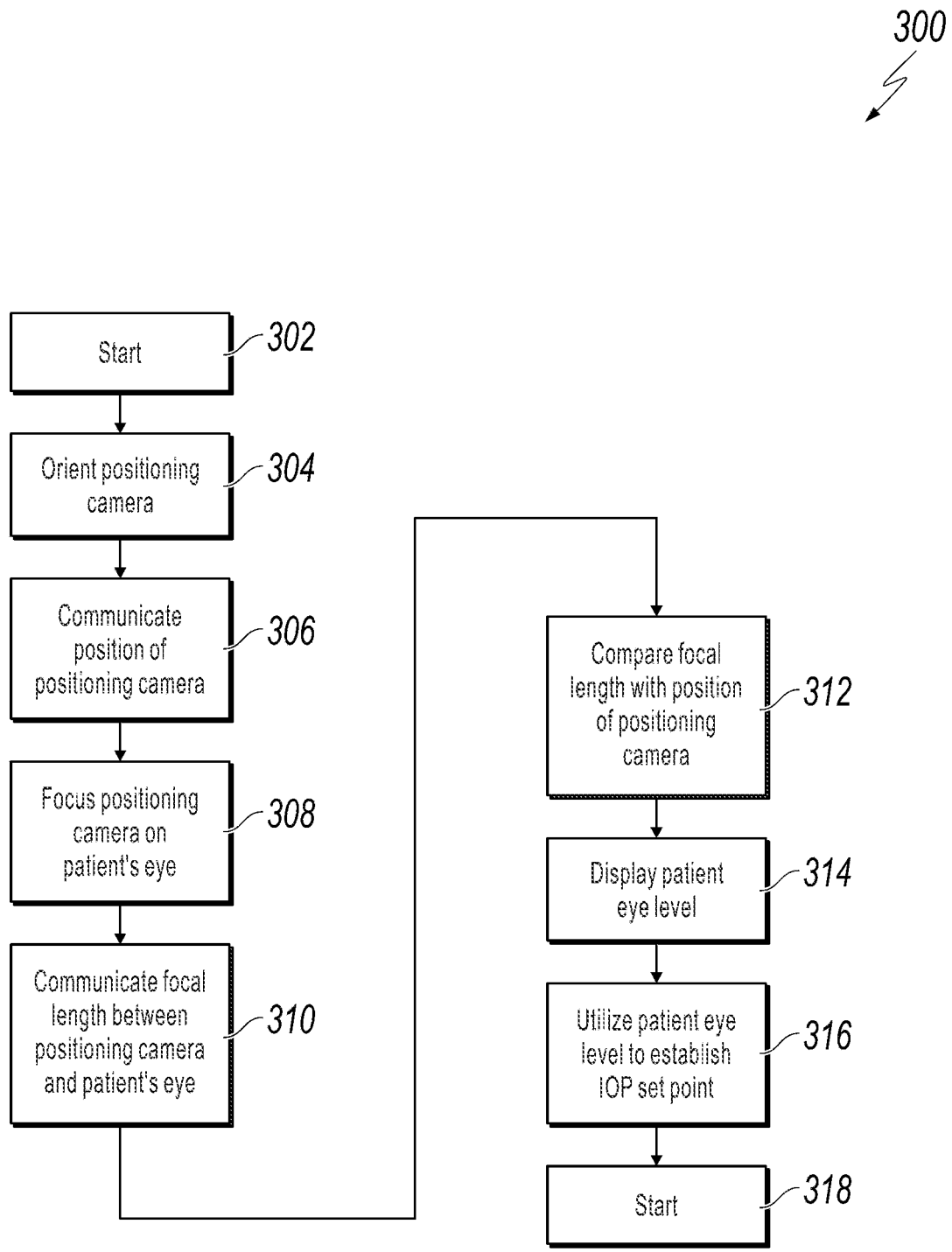
FIG. 3 is a flow diagram of a process for determining patient eye level according to aspects of the disclosure.

FIG. 3 is a flow diagram of a process 300 for determining patient eye level. The process 300 begins at step 302. At step 304, the positioning camera 204 is oriented above the eye 112 of the patient. At step 306, the encoder 207 communicates the position (h) of the positioning camera 204 relative to the fixed datum 216 to the processor 108. At step 308, the positioning camera 204 focuses on the patient's eye 112. At step 310, the focal length (z) of the positioning camera 204 is communicated to the processor 108. At step 312, the processor 108 compares the focal length (z) with the position (h) of the positioning camera 204 and determines the patient's eye level. At step 314, the patient's eye level is displayed to an operator via the display device 120. At step 316, the patient's eye level is utilized by the operator to establish the IOP set point. The process 300 ends at step 318. In various embodiments, however, the process 300 may periodically or continuously monitor the patient eye level in an effort to ensure proper regulation of IOP during the ophthalmic surgical intervention. In such embodiments, the process 300 does not end at step 318 but, rather, returns to step 308 from step 316.

Depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. Although certain computer-implemented tasks are described as being performed by a particular entity, other embodiments are possible in which these tasks are performed by a different entity.

For purposes of this patent application, the term computer-readable storage medium encompasses one or more tangible computer-readable storage media possessing structures. As an example and not by way of limitation, a computer-readable storage medium may include a semiconductor-based or other integrated circuit (IC) (such as, for example, a field-programmable gate array (FPGA) or an application-specific IC (ASIC)), a hard disk, an HDD, a hybrid hard drive (HHD), an optical disc, an optical disc drive (ODD), a magneto-optical disc, a magneto-optical drive, a floppy disk, a floppy disk drive (FDD), magnetic tape, a holographic storage medium, a solid-state drive (SSD), a RAM-drive, a SECURE DIGITAL card, a SECURE DIGITAL drive, a flash memory card, a flash memory drive, or any other suitable tangible computer-readable storage medium or a combination of two or more of these, where appropriate.

The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," "generally," and "about" may be substituted with "within [a percentage] of" what is specified.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the devices illustrated can be made without departing from the spirit of the disclosure. As will be recognized, the processes described herein can be embodied within a form that does not provide all of the features and benefits set forth herein, as some features can be used or practiced separately from others. The scope of protection is defined by the appended claims rather than by the foregoing description. All changes which come within the meaning and range of equivalency of the claims are to be embraced within their scope.

What is claimed is:

1. An ophthalmic surgical system, comprising:
   a robotic arm disposed above a patient's eye;
   a positioning camera disposed on the robotic arm and positioned to visualize the patient's eye;
   a processor electrically coupled to the positioning camera, the processor being configured to:
      receive an indication of a position of the robotic arm relative to a fixed datum;
      determine a focal length between the positioning camera and the patient's eye;
      determine a patient eye level relative to the fixed datum by comparing the focal length to the position of the robotic arm; and
      determine an intraocular pressure set point based on the patient eye level.

2. The ophthalmic surgical system of claim 1, wherein the fixed datum is a floor of a surgical suite.

3. The ophthalmic surgical system of claim 2, wherein the position of the robotic arm relative to the fixed datum is a height of the robotic arm above the floor of the surgical suite.

4. The ophthalmic surgical system of claim 2, wherein the patient eye level relative to the fixed datum is a height of the patient's eye above the floor.

5. The ophthalmic surgical system of claim 1, wherein the positioning camera is a three-dimensional stereoscopic camera.

6. The ophthalmic surgical system of claim 1, comprising an encoder coupled to the robotic arm, the encoder being configured to determine a position of the robotic arm relative to the fixed datum.

7. The ophthalmic surgical system of claim 6, wherein the encoder is electrically coupled to the processor.

8. The ophthalmic surgical system of claim 7, wherein the encoder is at least one of a linear encoder and an angular encoder.

9. A surgical microscope, comprising:
   a positioning camera positioned to visualize a patient's eye;
   an encoder coupled to the positioning camera, the encoder being configured to determine a position of the positioning camera relative to a fixed datum;
   a processor electrically coupled to the encoder and the positioning camera, the processor being configured to:
      receive an indication of a position of the positioning camera relative to the fixed datum;
      determine a focal length between the positioning camera and the patient's eye;
      determine a patient eye level relative to the fixed datum by comparing the focal length to the position of the positioning camera; and
      determine an intraocular pressure set point based on the patient eye level.

10. The surgical microscope of claim 9, wherein the fixed datum is a floor of a surgical suite.

11. The surgical microscope of claim 10, wherein the position of the positioning camera relative to the fixed datum is a height of the positioning camera above the floor of the surgical suite.

12. The surgical microscope of claim 11, wherein the patient eye level relative to the fixed datum is a height of the patient's eye above the floor.

13. The surgical microscope of claim 9, wherein the positioning camera is a three-dimensional, stereoscopic camera.

14. The surgical microscope of claim 9, wherein the encoder is at least one of a linear encoder and an angular encoder.

15. A method of determining patient eye level, the method comprising:
   focusing a positioning camera on a patient's eye;
   determining a position of the positioning camera relative to a fixed datum;
   determining a focal length between the positioning camera and the patient's eye;
   determining the patient eye level by comparing the focal length to the position of the positioning camera relative to the fixed datum; and
   determining an intraocular pressure set point based on the patient eye level.

16. The method of claim 15, wherein the determining the position of the positioning camera relative to the fixed datum comprises determining a height of the positioning camera above a floor of a surgical suite.

17. The method of claim 16, wherein the patient eye level is a height of the patient's eye above the floor of the surgical suite.

18. The method of claim 15, wherein the determining the focal length is performed continuously.

19. The method of claim 18, wherein continuous determination of the focal length facilitates adjustment of the intraocular pressure set point during an ophthalmic surgical intervention.

* * * * *